(12) United States Patent
Kusano et al.

(10) Patent No.: US 10,485,889 B2
(45) Date of Patent: Nov. 26, 2019

(54) STERILIZING CASE

(71) Applicants: CREATIVE TECHNOLOGY CORPORATION, Kawasaki-shi, Kanagawa (JP); MATSUDA DESIGN LTD, Tokyo (JP)

(72) Inventors: Mutsumi Kusano, Kawasaki (JP); Yoshiaki Tatsumi, Kawasaki (JP); Li Luo, Kawasaki (JP); Kazuki Tsuboi, Kawasaki (JP); Satomi Koyama, Kawasaki (JP); Takeshi Matsuda, Tokyo (JP); Shujiro Hayashi, Tokyo (JP)

(73) Assignees: CREATIVE TECHNOLOGY CORPORATION, Kawasaki-Shi, Kanagawa (JP); MATSUDA DESIGN LTD, Tokyo (JP)

( * ) Notice: Subject to any disclaimer, the term of this patent is extended or adjusted under 35 U.S.C. 154(b) by 200 days.

(21) Appl. No.: 15/568,288

(22) PCT Filed: May 19, 2016

(86) PCT No.: PCT/JP2016/064890
§ 371 (c)(1),
(2) Date: Oct. 20, 2017

(87) PCT Pub. No.: WO2016/186168
PCT Pub. Date: Nov. 24, 2016

(65) Prior Publication Data
US 2018/0169282 A1 Jun. 21, 2018

(30) Foreign Application Priority Data
May 21, 2015 (JP) .................................. 2015-104000

(51) Int. Cl.
*A61L 2/20* (2006.01)
*A61L 2/26* (2006.01)
(Continued)

(52) U.S. Cl.
CPC ................. *A61L 2/202* (2013.01); *A61L 2/26* (2013.01); *C01B 13/115* (2013.01);
(Continued)

(58) Field of Classification Search
CPC ... A61L 2/202; A61L 2/20; A61L 2/26; A61L 2202/11; A61L 2/10; A61L 2/24;
(Continued)

(56) References Cited

U.S. PATENT DOCUMENTS 6,490,351 B1 * 12/2002 Roberts ..................... A61L 2/10
379/439
7,289,628 B2 * 10/2007 Lin .......................... H04M 1/17
379/439
(Continued)

FOREIGN PATENT DOCUMENTS

| CN | 2262029 Y | 9/1997 |
| CN | 1365289 A | 8/2002 |

(Continued)

OTHER PUBLICATIONS

PCT, "International Search Report for International Application No. PCT/JP2016/064890" dated Jun. 28, 2016.
(Continued)

*Primary Examiner* — Xiuyu Tai
(74) *Attorney, Agent, or Firm* — Manabu Kanesaka

(57) ABSTRACT

A sterilization case can be reduced, and it is possible to reliably sterilize not only the surface of a mobile communication device but hidden portions thereof as well. A sterilization case includes a case main body and a cover body. The case main body includes a voltage supplying part
(Continued)

and a loading part having an electrode sheet. The voltage supplying part includes a boosting circuit, a direct-current conversion circuit, a switch circuit, and a sterilization meter. The boosting circuit supplies the voltage necessary to generate ozone to the electrode sheet. The direct-current conversion circuit performs conversion to a power source voltage of a smartphone as the mobile communication device and outputs to a male connector. The male connector can be connected to a female connector of the smartphone. The cover body is attached to the case main body so as to be able to open and close.

13 Claims, 17 Drawing Sheets

(51) Int. Cl.
*C01B 13/11* (2006.01)
*H02J 7/00* (2006.01)
*H04M 1/02* (2006.01)

(52) U.S. Cl.
CPC ....... *A61L 2202/11* (2013.01); *C01B 2201/22* (2013.01); *C01B 2201/32* (2013.01); *C01B 2201/34* (2013.01); *H02J 7/0042* (2013.01); *H04M 1/0262* (2013.01)

(58) Field of Classification Search
CPC ............ A61L 2202/16; A61L 2202/14; A61L 2202/122; A45C 11/00; C01B 13/11; C01B 13/115; C01B 2201/22; C01B 2201/32; C01B 2201/34; H02J 7/00; H02J 7/0042; H05K 5/02; H01M 10/44; H04M 1/0262; H04M 1/17; H04M 1/72527; H04M 1/04; H04M 9/00; H04M 1/00; B22C 1/34; B22C 1/22; H01J 37/08; H01J 37/32; H04R 1/12
See application file for complete search history.

(56) References Cited

U.S. PATENT DOCUMENTS

| | | | |
|---|---|---|---|
| 7,424,314 B2* | 9/2008 | Park | H04M 1/17 379/452 |
| 7,438,870 B2 | 10/2008 | Anno | |
| 8,481,970 B2* | 7/2013 | Cooper | A61L 2/10 250/453.11 |
| 9,536,709 B2 | 1/2017 | Koyama et al. | |
| 2013/0063922 A1 | 3/2013 | La Porte et al. | |

FOREIGN PATENT DOCUMENTS

| | | |
|---|---|---|
| CN | 100389835 C | 5/2008 |
| CN | 201516177 U | 6/2010 |
| CN | 203507169 U | 4/2014 |
| JP | H07-309605 A | 11/1995 |
| JP | H09-220275 A | 8/1997 |
| JP | 2000-219503 A | 8/2000 |
| JP | 2004-201788 A | 7/2004 |
| JP | 2006-066857 A | 3/2006 |
| JP | 2013-236120 A | 11/2013 |
| JP | 2013-236414 A | 11/2013 |
| JP | 2014-68484 A | 4/2014 |
| JP | 2014-158217 A | 8/2014 |
| KR | 20-2008-0000274 U | 3/2008 |
| WO | 2014/119349 A1 | 8/2014 |

OTHER PUBLICATIONS

Europe Patent Office, "Search Report for European Patent Publication No. 16796561.5," dated Oct. 17, 2018.
China Patent Office, "Office Action for Chinese Patent Publication No. 201680022491.7," dated Jul. 2, 2019.

* cited by examiner

STERILIZING CASE

RELATED APPLICATIONS

The present application is National Phase of International Application No. PCT/JP2016/064890 filed May 19, 2016, and claims priority from Japanese Application No. 2015-104000, filed May 21, 2015, the disclosure of which is hereby incorporated by reference herein in its entirety.

TECHNICAL FIELD

The present invention relates to a sterilization case for sterilizing a mobile communication device such as a smartphone.

BACKGROUND ART

For example, a smartphone serving as a mobile communication device can be wiped and cleaned on its surface with a cloth-like material. The smartphone is not only cleaned but then also sterilized generally through a wiping operation with cleaner and/or disinfectant such as alcohol.

However, in this sterilization method, the smartphone must be wiped manually, which requires a great deal of time and effort. In addition, if disinfectant or the like adheres to the hands, there is a concern that this may cause a rash.

There has hence been proposed a sterilization apparatus described in Patent Literature 1, for example, as a technique capable of sterilizing a smartphone without a need for such a wiping operation.

The sterilization apparatus has a structure serving as a charger for the smartphone as well as a sterilizer. Specifically, the smart phone is housed in the casing of the apparatus and the charging terminal of the smartphone is connected to the connector of the apparatus so that the smartphone is supplied with electric power. Moreover, an ultraviolet lamp is provided inside the casing and, during charging, the smartphone is irradiated with ultraviolet light from the lamp and thereby sterilized.

CITATION LIST

Patent Literature

PLT 1: Japanese Application Laid-Open No. 2014-068484

SUMMARY OF THE INVENTION

Technical Problem

However, the above-described conventional technique suffers from the following problems.

That is, the above-described sterilization apparatus can sterilize only a portion of the smartphone irradiated with ultraviolet light. Thus, the side surface and gaps of the smartphone, which are less likely to be irradiated with ultraviolet light, are not sterilized sufficiently. To address this, in order for the apparatus to have a structure in which all the surfaces of the smartphone including the side surface can be sterilized, portions inside the apparatus opposed to all the surfaces, i.e., the upper surface, the lower surface, and the side surface of the smartphone must be equipped with ultraviolet lamps. Accordingly, the apparatus itself must be increased in size to have a structure in which all the surfaces of the smartphone can be sterilized. As a result, a problem of an increase in the size and weight of the apparatus occurs.

In the case of a smartphone with accessories and/or cases attached thereto, portions hidden behind these accessories, etc., cannot be sterilized with such a light-based technique.

The present invention has been made to solve the above-described problems, and an object thereof is to provide a sterilization case whereby the size of the case itself can be reduced, and it is possible to reliably sterilize not only the surface of a mobile communication device but also hidden portions thereof as well, the amount of space used for sterilization of the mobile communication device can be reduced, and charging and sterilization can be performed simultaneously.

Solution to the Problems

In order to solve the above-described problems, the invention of claim 1 is directed to a sterilization case including: a case main body having a loading part with a surface on which an electrode sheet is laid, the electrode sheet formed by housing at least one of a pair of electrodes within a sheet-like dielectric, and in which a mobile communication device can be loaded on the electrode sheet and a voltage supplying part for supplying a predetermined voltage to the electrode sheet and the mobile communication device; and a cover body attached to the case main body in an openable and closable manner, in which the voltage supplying part includes: a first circuit for converting a power source into a voltage necessary to generate ozone and supplying the voltage to the pair of electrodes; and a second circuit for converting the power source into a power source voltage of the mobile communication device and supplying the power source voltage to a male connector connectable to a female connector for power supply to the mobile communication device.

With the arrangement above, the mobile communication device is loaded on the electrode sheet of the case main body with the cover body being opened and the male connector of the second circuit of the voltage supplying part is connected to the female connector for power supply to the mobile communication device.

After closing the cover body, when the power source is turned on, the first circuit of the voltage supplying part supplies a voltage necessary to generate ozone to the pair of electrodes of the electrode sheet. As a result, ozone is emitted from the electrode sheet to sterilize the mobile communication device loaded on the electrode sheet.

In parallel, the second circuit converts the power source into a power source voltage of the mobile communication device and supplies the power source voltage to the mobile communication device through the male connector and the female connector for power supply to the mobile communication device. As a result, the mobile communication device is charged.

The sterilization case according to the present invention thus allows for sterilization with ozone and charging at one time. That is, it is no longer necessary to perform a separate sterilizing operation for the mobile communication device, which requires extra time and effort, but a sterilizing operation can be performed automatically as part of the routine of the regular charging operation.

In addition, since gaseous ozone is emitted with the mobile communication device being confined within the sterilization case, the sterilization case is filled with ozone. As a result, the ozone wraps around the entire mobile communication device to sterilize not only the surface of the mobile communication device but also portions hidden behind the accessories, etc.

Further, while ceramic is commonly used as a material of ozone generators, using such an electrode sheet as in the present invention as an ozone generator allows ozone to be emitted and blown directly onto the surfaces of the mobile communication device. As a result, the amount of ozone generation per unit area from the electrode sheet can be smaller than the amount of ozone generation per unit area from ceramic. As a result, the amount of consumption of the power source for driving the ozone generator can be reduced to save energy.

After completion of the sterilization, the power source is then turned off and the cover body is opened, whereby the mobile communication device can be taken out of the case main body.

In addition, the sterilization case according to the present invention, which is constituted by the case main body for housing the mobile communication device therein and the cover body, can be close in overall size to the size of the mobile communication device, and it is therefore possible to reduce the size and weight of the case itself. As a result, the sterilizing operation can be made even in such a small operation space.

Further, the electrode sheet itself, which is arranged to be laid within the case main body, is in a thin sheet form and therefore cannot increase the size of the sterilization case.

The invention of claim 2 is directed to the sterilization case according to claim. 1, in which an electrode sheet separate from the electrode sheet is provided on the inner surface of the top wall of the cover body, and in which the first circuit is connected also to a pair of electrodes of the separate electrode sheet.

With the arrangement above, ozone can be emitted from both above and below the mobile communication device. As a result, the sterilization time for the mobile communication device can be shortened.

The invention of claim 3 is directed to the sterilization case according to claim. 1 or 2, in which a spacer for loading the mobile communication device is provided in a manner protruding on the electrode sheet on the loading part.

With the arrangement above, a large amount of air gains entrance also under the mobile communication device, and thereby the rate of ozone generation by the electrode sheet increases. This can result in an increase in the sterilization effect.

The invention of claim 4 is directed to the sterilization case according to claim 1 or 2, in which the loading part is formed to have a waved cross-sectional shape and the electrode sheet is laid along the waved loading part.

With the arrangement above, the gap between the waved loading part and the mobile communication device is filled with a large amount of air, and thereby the rate of ozone generation by the electrode sheet increases. This can result in an increase in the sterilization effect. Further, since the loading part is formed not in a planar shape but in a waved shape and the electrode sheet is laid along the loading part, the area of the electrode sheet can be increased.

The invention of claim 5 is directed to the sterilization case according to any one of claims 1 to 4, in which the power source is an alternate-current power source, and in which the first circuit is a circuit for converting the alternate-current voltage of the power source into an alternate-current voltage or a pulsed voltage of a desired value and supplying the voltage to the pair of electrodes, and in which the second circuit is a circuit for converting the alternate-current voltage of the power source into a direct-current voltage of a desired value and supplying the voltage to the male connector.

With the arrangement above, when the power source is supplied to the voltage supplying part, the first circuit converts the alternate-current voltage of the power source into an alternate-current voltage or a pulsed voltage of a desired value and supplies the voltage to the pair of electrodes. At the same time, the second circuit converts the alternate-current voltage of the power source into a direct-current voltage of a desired value and supplies the voltage to the male connector.

The invention of claim 6 is directed to the sterilization case according to any one of claims 1 to 4, in which the power source is a direct-current power source, and in which the first circuit is a circuit for converting the direct-current voltage of the power source into an alternate-current voltage or a pulsed voltage of a desired value and supplying the voltage to the pair of electrodes, and in which the second circuit is a circuit for converting the direct-current voltage of the power source into a direct-current voltage of a desired value and supplying the voltage to the male connector.

With the arrangement above, when the power source is supplied to the voltage supplying part, the first circuit converts the direct-current voltage of the power source into an alternate-current voltage or a pulsed voltage of a desired value and supplies the voltage to the pair of electrodes. At the same time, the second circuit converts the direct-current voltage of the power source into a direct-current voltage of a desired value and supplies the voltage to the male connector.

The invention of claim 7 is directed to the sterilization case according to claim 6, in which the second circuit is a circuit for supplying the direct-current voltage of the power source directly to the male connector.

With the arrangement above, the second circuit supplies the direct-current voltage of the power source directly to the male connector.

The invention of claim 8 is directed to the sterilization case according to any one of claims 1 to 7, in which at least the dielectric of the electrode sheet is formed of polymeric resin.

With the arrangement above, the electrode sheet, in which at least the dielectric is formed of polymeric resin, can generate ozone.

While ceramic is commonly used as a material of ozone generators, using such a polymeric resin sheet as in the present invention as an ozone generator allows the thickness and weight of the electrode sheet to be reduced and the area of the ozone generation part to be increased as well as, due to its flexibility, the electrode sheet to be laid in a manner following the shape of the loading part of the case main body even if the loading part may be curved, for example.

The invention of claim 9 is directed to the sterilization case according to any one of claims 1 to 8, in which a switch mechanism is provided on the case main body, the switch mechanism capable of turning the power source on only when the cover body is closed and turning the power source off after a predetermined period of sterilization time with the power source on.

With the arrangement above, when the mobile communication device is housed within the case main body and the cover body is then closed, the power source is turned on by the switch mechanism. This causes the housed mobile communication device to be sterilized automatically. When the sterilization is completed after a predetermined period of sterilization time, the power source is turned off by the switch mechanism.

The invention of claim 10 is directed to the sterilization case according to any one of claims 1 to 9, in which a sterilization meter for displaying sterilization processing time is provided on the case main body.

With the arrangement above, the sterilization processing time can be roughly visualized by the sterilization meter to be checked and it is therefore possible to feel a real sense of sterilization accomplishment.

The invention of claim 11 is directed to the sterilization case according to any one of claims 1 to 10, in which the pair of electrodes are each formed in a comb shape and the comb teeth of the pair of electrodes are engaged with each other at a regular interval.

With the arrangement above, a discharge phenomenon occurs between the pair of electrodes, in which the comb teeth are engaged with each other at a regular interval, whereby ozone is generated.

The invention of claim 12 is directed to the sterilization case according to any one of claims 1 to 10, in which one of the pair of electrodes is housed within the dielectric and the other electrode with a number of holes or in a comb shape is disposed on the surface of the dielectric in a manner opposed to the one electrode.

The invention of claim 13 is directed to the sterilization case according to any one of claims 1 to 12, in which the loading part is provided with a maintaining part for maintaining the distance between the electrode sheet and the mobile communication device or the case of the mobile communication device loaded on the loading part within a range of 10 mm or less.

With the arrangement above, even a mobile communication device having a textured surface or a mobile communication device with a case made of textured material or cloth can be sterilized reliably.

Effects of the Invention

As described in detail hereinbefore, the sterilization case according to the present invention thus allows for sterilization with ozone and charging of the mobile communication device at one time in a very useful way.

The arrangement of sterilization not with light but with gaseous ozone also allows not only the surface but also hidden portions of the mobile communication device to be sterilized.

In addition, the sterilization case according to the present invention can be close in overall size to the size of the mobile communication device, and it is therefore possible to reduce the size and weight of the case itself.

Particularly, in accordance with the invention of claim 2, the sterilization time for the mobile communication device can be shortened.

Also, in accordance with the invention of claim 3, the rate of ozone generation and therefore the sterilization effect can be increased.

Also, in accordance with the invention of claim 4, the rate of ozone generation can be further increased.

Also, in accordance with the invention of claim 8, further size reduction can be achieved.

In accordance with the inventions of claims 9 and 10, the power source can be turned off automatically after completion of the sterilization and the sterilization processing time can be roughly visualized for checking in a very useful way.

DESCRIPTION OF THE EMBODIMENTS

The best mode of the present invention will hereinafter be described with reference to the accompanying drawings.

First Embodiment

Figure 1:
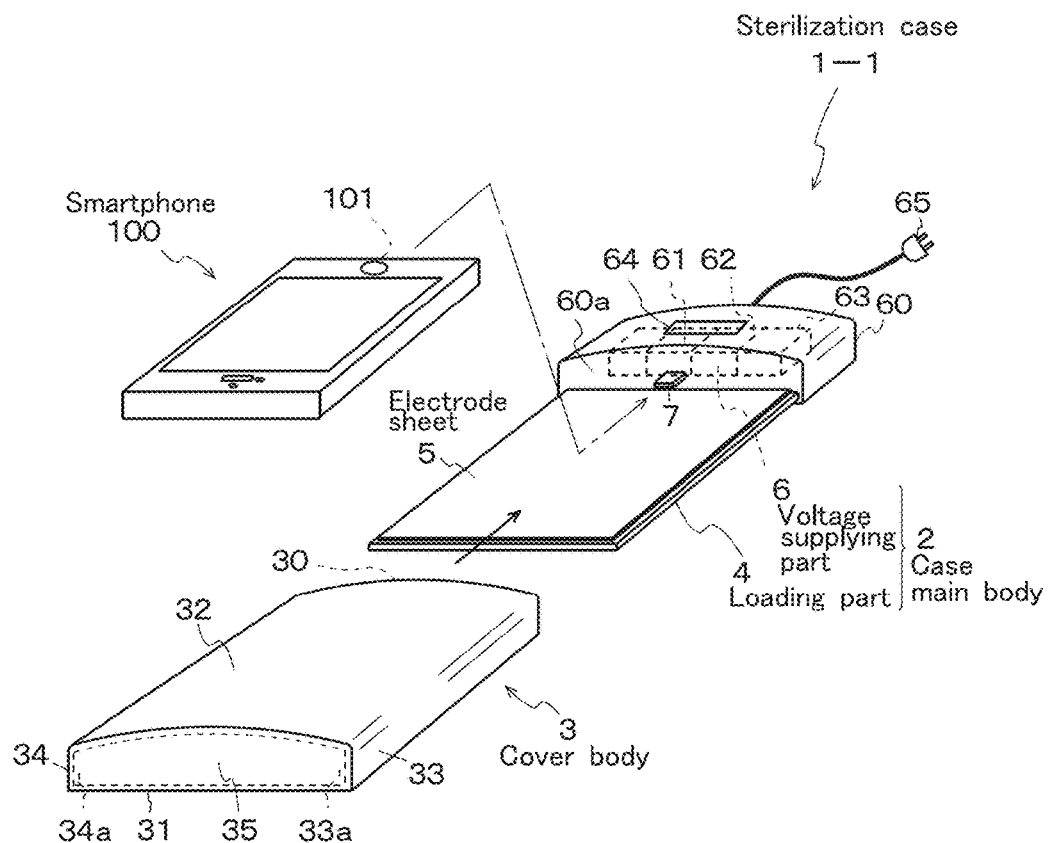
FIG. 1 is an exploded perspective view of a sterilization case according to a first embodiment of the present invention.

FIG. 1 is an exploded perspective view of a sterilization case according to a first embodiment of the present invention.

As shown in FIG. 1, the sterilization case 1-1 according to this embodiment includes a case main body 2 and a cover body 3.

Figure 2:
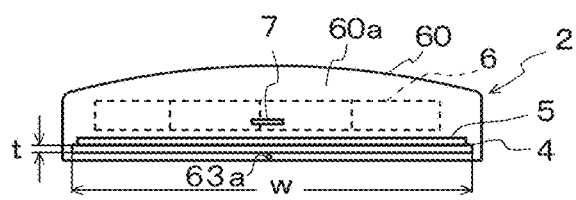
FIG. 2 is a front view of a case main body.

FIG. 2 is a front view of the case main body 2.

As shown in FIGS. 1 and 2, the case main body 2 is a base for setting a smartphone 100 serving as a mobile communication device thereon, including a loading part 4 and a voltage supplying part 6.

The loading part 4 is a rectangular plate body with a thickness "t" and a width "w", on the surface thereof is laid an electrode sheet 5 on which the smartphone 100 can be loaded.

The electrode sheet 5 is a flexible sheet that generates ozone.

Figure 3:
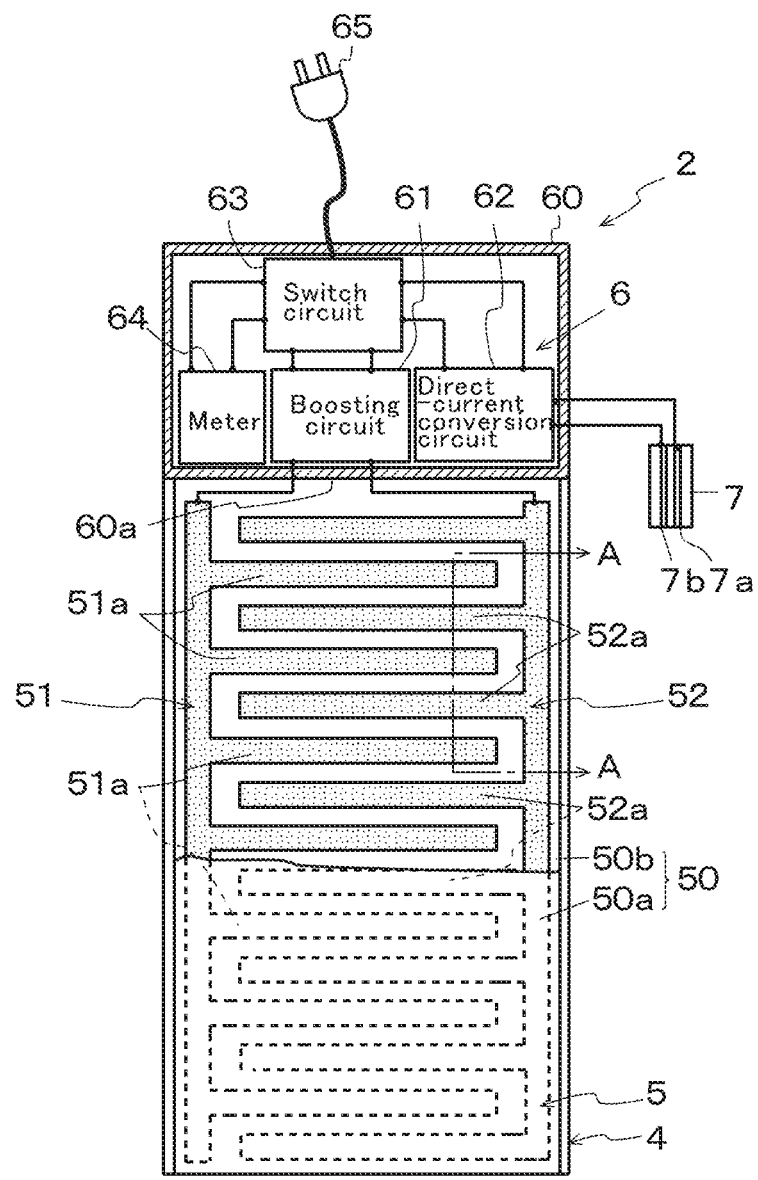
FIG. 3 is a cutaway schematic plan view of the case main body.
Figure 4:
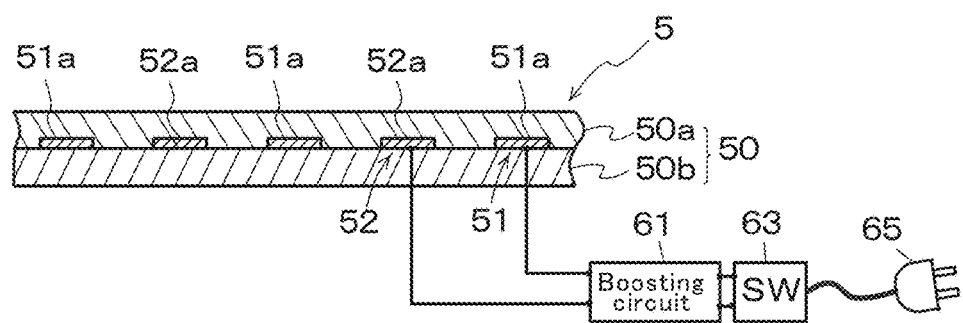
FIG. 4 is a cross-sectional view indicated by the arrows A-A in FIG. 3.

FIG. 3 is a cutaway schematic plan view of the case main body 2, and FIG. 4 is a cross-sectional view indicated by the arrows A-A in FIG. 3.

As shown in FIGS. 3 and 4, the electrode sheet 5 is formed by a sheet-like dielectric 50 and a pair of electrodes 51, 52 housed within the dielectric 50.

Specifically, as shown in FIG. 4, the dielectric 50 is formed of two dielectric layers 50a, 50b, in which the electrodes 51, 52 are formed on the lower dielectric layer 50b and the upper dielectric layer 50a is laminated on the dielectric layer 50b in a manner covering the electrodes 51, 52.

The thus arranged electrode sheet 5 is entirely formed of polymeric resin. In this embodiment, not only are the dielectric layers 50a, 50b respectively formed of polyimide resin, but the electrodes 51, 52 are also formed of conductive polymer, an example of polymeric resin. The electrode sheet 5 thus entirely formed of polymeric resin has increased flexibility as well as reduced thickness and weight of the electrode sheet 5, and allows the area of the ozone generation part of the electrode sheet 5 to be increased.

Further, as shown in FIG. 3, the pair of electrodes 51, 52 are each formed in a comb shape and the comb teeth 51a, 52a are engaged with each other at a regular interval.

The voltage supplying part 6 is arranged to supply a predetermined voltage to the electrode sheet 5 and the smartphone 100.

Specifically, as shown in FIG. 3, the voltage supplying part 6 is housed within a housing part 60 that is disposed on the rear end side of the loading part 4 (upper end side in FIG. 3).

The voltage supplying part 6 includes a boosting circuit 61 serving as a first circuit, a direct-current conversion circuit 62 serving as a second circuit, a switch circuit 63 serving as a switch mechanism, and a sterilization meter 64.

The boosting circuit 61 is a circuit for converting the power source voltage into a voltage necessary to generate ozone and supplying the voltage to the electrodes 51, 52 of the electrode sheet 5.

Specifically, in this embodiment, a commercial alternate-current voltage power source 65 of 100 V is used as the power source, and the boosting circuit 61 is connected electrically to the power source 65 via the switch circuit 63.

The boosting circuit 61 has a function of boosting the alternate-current voltage of 100 V input from the power source 65 to an alternate-current voltage or a pulsed voltage of, for example, 2 kV to 10 kV and supplying the voltage to the electrodes 51, 52 of the electrode sheet 5.

The direct-current conversion circuit 62 is a circuit for converting the alternate-current voltage power source 65 into a power source voltage of the smartphone 100 (see FIG. 1) and supplying the power source voltage to a male connector 7.

Specifically, like the boosting circuit 61, the direct-current conversion circuit 62 is also connected electrically to the power source 65 via the switch circuit 63. The direct-current conversion circuit 62 has a function of converting the alternate-current voltage of 100 V input from the power source 65 to a direct-current voltage of, for example, 5 V and supplying the voltage to the male connector 7.

As shown in FIGS. 1 and 2, the male connector 7 is provided in a protruding manner in the central and lower part of the front wall 60a of the housing part 60. In a detailed arrangement, when the smartphone 100 is loaded on the electrode sheet 5 of the loading part 4, a female connector 101 provided in the rear surface of the smartphone 100 can be connected to the male connector 7. As shown FIG. 3, the male connector 7 is also provided with power source terminals 7a, 7b and, when the male connector 7 is connected to the female connector 101, the power source terminals 7a, 7b are to be in contact with power source terminals (not shown) of the female connector.

The switch circuit 63 is a circuit for connecting or disconnecting the power source 65 to/from the boosting circuit 61, the direct-current conversion circuit 62, and the sterilization meter 64.

Figure 5:
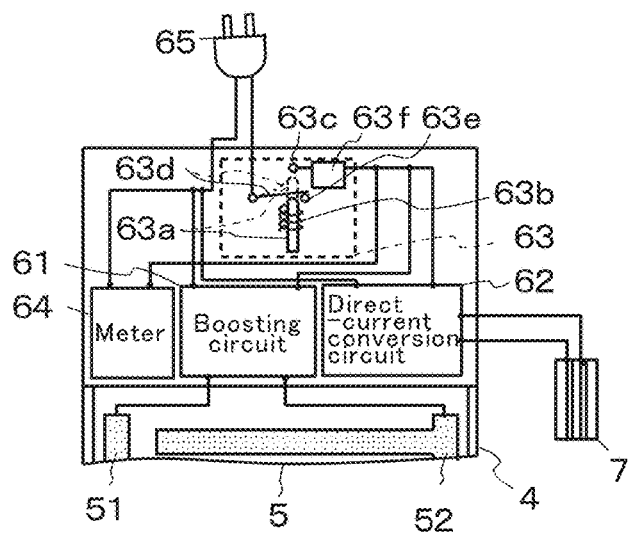
FIG. 5 is a schematic view showing the structure of a switch circuit.
Figure 6:
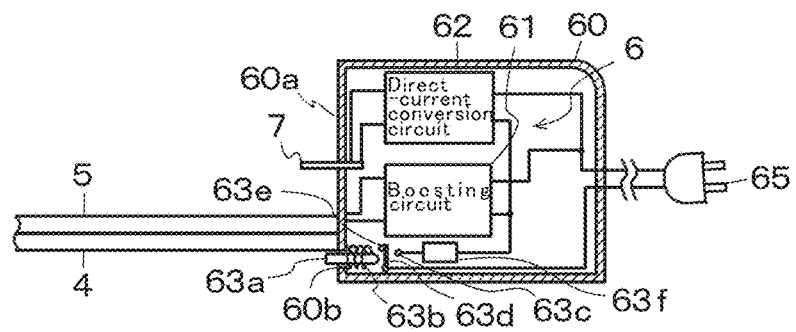
FIG. 6 is a side view showing an arrangement state of a pin body of the switch circuit.

FIG. 5 is a schematic view showing the structure of the switch circuit 63, and FIG. 6 is a side view showing an arrangement state of a pin body of the switch circuit 63.

As shown in FIG. 5, the switch circuit 63 includes a pin body 63a, a spring 63b, a fixed terminal 63c, and a movable terminal 63d.

As shown in FIG. 6, the leading end of the pin body 63a is inserted through a hole 60b provided in the front wall 60a of the housing part 60. Moreover, the spring 63b is interposed between the pin body 63a and the housing part 60 to urge the pin body 63a to protrude outward from the front wall 60a.

On the other hand, as shown in FIG. 5, the fixed terminal 63c is connected electrically to one of the input terminals of each of the boosting circuit 61, the direct-current conversion circuit 62, and the sterilization meter 64, while the movable terminal 63d is connected electrically to one of the output terminals of the power source 65. The movable terminal 63d is a plate-spring-like metal body and, when not subject to an external force, in pressure contact with a stopper 63e from the rear (top in FIG. 5, right in FIG. 6) toward the front (bottom in FIG. 5, left in FIG. 6) of the housing part 60. Accordingly, the movable terminal 63d, when not subject to a pressing force from the pin body 63a, is not in contact with the fixed terminal 63c. However, when the pin body 63a moves rearward to press the movable terminal 63d rearward as indicated by the broken line, the movable terminal 63d comes into contact with the fixed terminal 63c.

That is, the switch circuit 63 has a function of connecting or disconnecting the commercial power source 65 depending on the movement of the pin body 63a.

The switch circuit 63 further has a function of turning the power source off after a predetermined period of time with the power source on.

Specifically, a controller 63f is provided at a stage subsequent to the fixed terminal 63c. The controller 63f incorporates a timer (not shown) and, when the power source is turned on, activates the timer. Based on the time passage of the timer, the controller 63f then disconnects the fixed terminal 63c electrically from the boosting circuit 61, the direct-current conversion circuit 62, and the sterilization meter 64 after a predetermined period of time. When the power source is turned off, the controller 63f then resets the timer and again connects the fixed terminal 63c electrically to the boosting circuit 61, the direct-current conversion circuit 62, and the sterilization meter 64.

The sterilization meter 64 is a device for displaying sterilization processing time.

Figure 7:
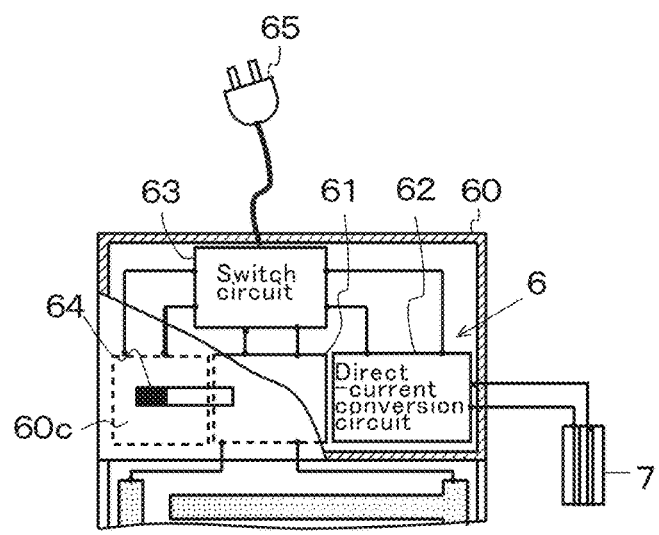
FIG. 7 is a schematic cross-sectional view of a sterilization meter.

FIG. 7 is a schematic cross-sectional view of the sterilization meter 64.

As shown in FIG. 7, the sterilization meter 64 is mounted on the top wall 60c of the housing part 60 while being connected electrically to the power source 65 via the switch circuit 63. This causes, when the switch circuit 63 is closed and thereby the power source is turned on, the sterilization meter 64 to be activated to display sterilization processing time.

On the other hand, as shown in FIG. 1, the cover body 3 is a box body fittable to the case main body 2 in an openable and closable manner and formed by a bottom wall 31, a top wall 32, side walls 33, 34, and a front wall 35. Moreover, an opening 30 is provided in a face opposed to the case main body 2.

Figure 8:
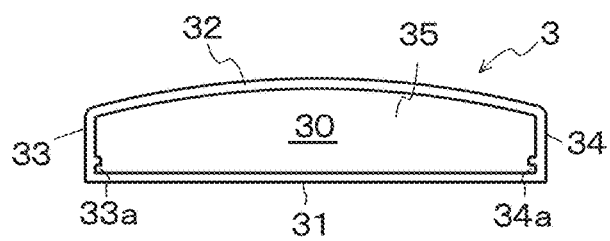
FIG. 8 is a front view of a cover body on the opening side.
Figure 9:
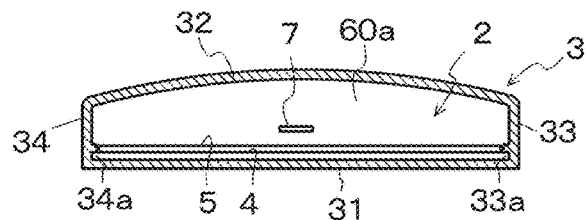
FIG. 9 is a cross-sectional view showing a state where the cover body is fitted to the case main body.

FIG. 8 is a front view of the cover body 3 on the opening 30 side, and FIG. 9 is a cross-sectional view showing a state where the cover body 3 is fitted to the case main body 2.

As shown in FIG. 8, the cover body 3 has a pair of grooves 33a, 34a.

Specifically, the groove 33a is formed at a corner between the side wall 33 and the bottom wall 31, while the groove 34a is formed at a corner between the side wall 34 and the bottom wall 31. The thus arranged grooves 33a, 34a are set to have a width (vertical width in FIG. 8) approximately equal to the thickness "t" of the loading part 4 of the case main body 2 (see FIG. 2) and a distance therebetween approximately equal to the width "w" of the loading part 4.

Since the cover body 3 has such a structure, the grooves 33a, 34a can be fitted slidably at the respective ends of the loading part 4 of the case main body 2 in a manner positioning the bottom wall 31 of the cover body 3 under the loading part 4, as shown in FIG. 9. Starting from this state, the cover body 3 can be slid toward the housing part 60 of the case main body 2 to be closed completely.

As mentioned above, the sterilization case 1-1 according to this embodiment can be close in overall size including the case main body 2 and the cover body 3 to the size of the smartphone 100, and it is therefore possible to reduce the size and weight of the sterilization case 1-1 itself.

Further, the thin electrode sheet 5, which is arranged to be laid within the case main body 2, cannot increase the size of the sterilization case 1-1.

Next will be described an example of how the sterilization case 1-1 according to this embodiment is used.

Figure 10A:
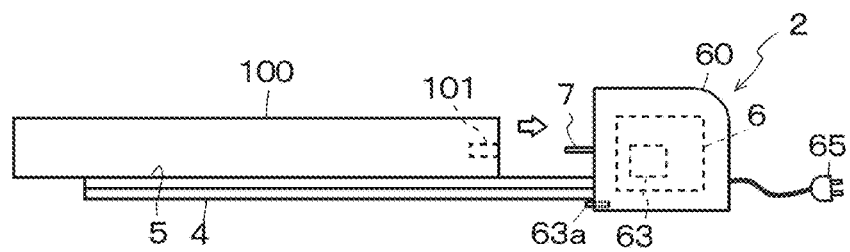
FIGS. 10(a), 10(b) and 10(c) are schematic side views showing examples of how the sterilization cases are used, where FIG. 10 (a) shows a state where a smartphone is loaded on the case main body, FIG. 10 (b) shows a state where the smartphone is connected electrically to the case main body, and FIG. 10 (c) shows a state where the cover body is closed.
Figure 10B:
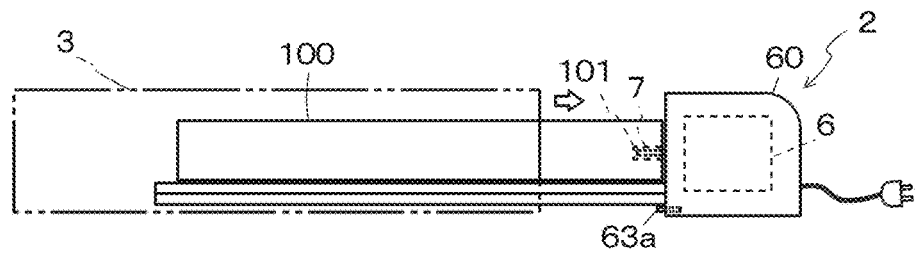
Figure 10C:
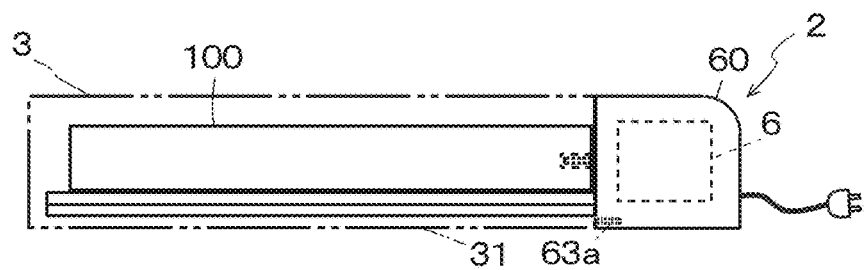
Figure 11:
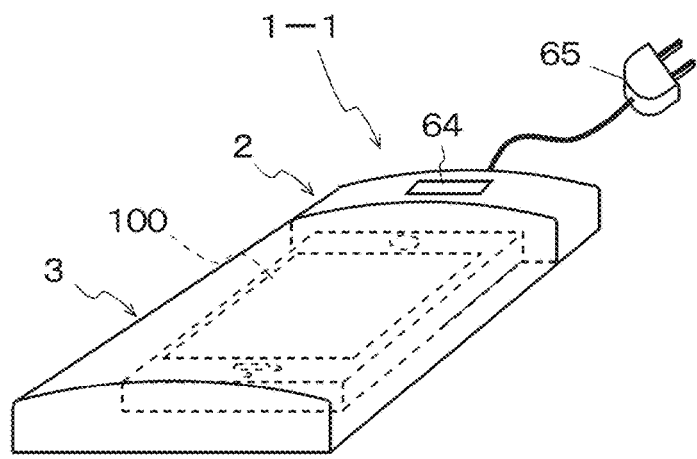
FIG. 11 is a perspective view showing a state where the smartphone is loaded on the case main body and the cover body is closed completely.

FIG. 10 is a schematic side view showing an example of how the sterilization case 1-1 is used, where FIG. 10 (a) shows a state where the smartphone 100 is loaded on the case main body 2, FIG. 10 (b) shows a state where the smartphone 100 is connected electrically to the case main body 2, and FIG. 10 (c) shows a state where the cover body 3 is closed. Also, FIG. 11 is a perspective view showing a state where the smartphone 100 is loaded on the case main body 2 and the cover body 3 is closed completely.

The smartphone 100 can be charged and sterilized as follows using the sterilization case 1-1 according to this embodiment.

First, in FIG. 10 (a), a user inserts the power source 65 of the case main body 2 into a commercial power source socket (not shown).

In this state, since the pin body 63a of the switch circuit 63 is not subject to an external pressing force, the movable terminal 63d is not in contact with the fixed terminal 63c as indicated by the solid line in FIG. 5, and the power source is in an off state. The commercial power source is therefore not input to the case main body 2.

In this state, as shown in FIG. 10 (a), the smartphone 100 is loaded on the electrode sheet 5 of the loading part 4, with the female connector 101 facing the male connector 7 of the case main body 2, and then moved toward the housing part 60. When the smartphone 100 is moved fully toward the housing part 60, the female connector 101 can be connected to the male connector 7 that protrudes from the housing part 60, as shown in FIG. 10 (b). That is, in this state, the smartphone 100 is connected electrically to the direct-current conversion circuit 62 (see FIG. 5) through the female connector 101 and the male connector 7.

Next, the cover body 3 is fitted to the loading part 4 as indicated by the alternate long and two short dashed line. Specifically, as shown in FIG. 9, the grooves 33a, 34a of the cover body 3 is fitted at the respective ends of the loading part 4 and the cover body 3 is slid toward the housing part 60 of the case main body 2.

When the cover body 3 is then moved fully toward the housing part 60 as shown in FIG. 10 (c), the cover body 3 is closed completely as shown in FIG. 11.

In this state, since the pin body 63a of the switch circuit 63 (see FIG. 5) is subject to a pressing force from the bottom wall 31 of the cover body 3 to move into the voltage supplying part 6 as shown in FIG. 10 (c), the movable terminal 63d comes into contact with the fixed terminal 63c as indicated by the broken line in FIG. 5. As a result, the power source is turned on and the commercial power source is input via the power source 65 and the switch circuit 63 to the boosting circuit 61, the direct-current conversion circuit 62, and the sterilization meter 64 for activation thereof.

Figure 12:
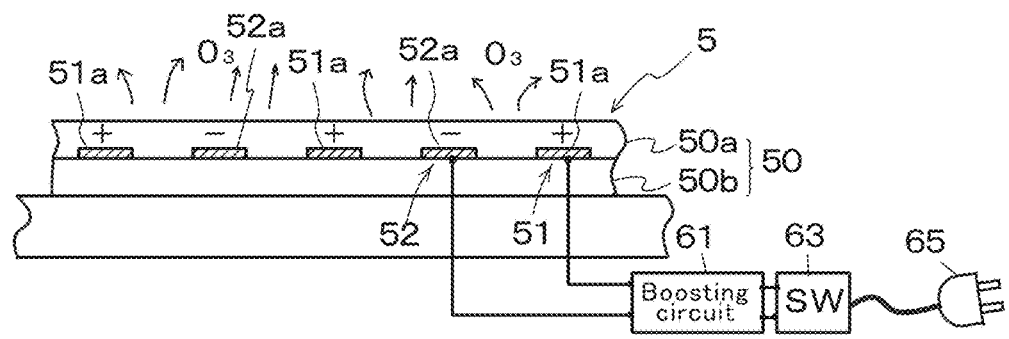
FIG. 12 is a schematic view showing a state where ozone is generated from an electrode sheet.

FIG. 12 is a schematic view showing a state where ozone is generated from the electrode sheet 5.

When the boosting circuit 61 is activated, the alternate-current voltage of 100 V input from the power source 65 at the commercial alternate-current voltage is boosted by the boosting circuit 61 to an alternate-current voltage or a pulsed voltage of 2 kV to 10 kV and supplied to the electrodes 51, 52 of the electrode sheet 5, as shown in FIG. 12. The polarity of the comb teeth 51a of the electrode 51 and the polarity of the comb teeth 52a of the electrode 52 then become opposite and thereby discharging occurs between the comb teeth 51a and 52a, so that ozone $O_3$ is generated. As a result, a large amount of ozone $O_3$ is emitted around the electrode sheet 5 as indicated by the arrows.

Figure 13:
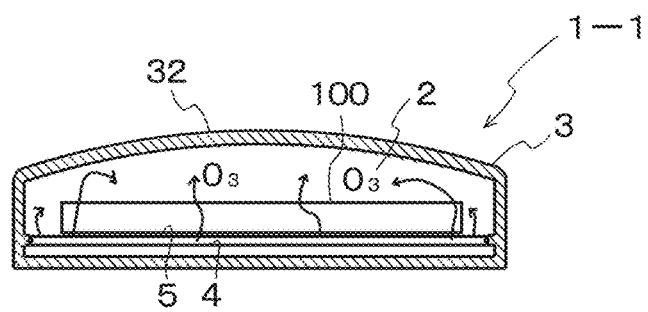
FIG. 13 is a cross-sectional view illustrating the sterilization mechanism of ozone.

FIG. 13 is a cross-sectional view illustrating the sterilization mechanism of ozone.

When a large amount of ozone $O_3$ is emitted around the electrode sheet 5 as mentioned above, the gaseous ozone $O_3$ is confined within the closed sterilization case 1-1 to fill the entire sterilization case 1-1, as shown in FIG. 13. As a result, the ozone $O_3$ will wrap around the entire smartphone 100 to sterilize not only the surface of the smartphone 100 but also portions hidden behind the accessories, etc.

In this state, as shown in FIG. 11, the sterilization processing time, that is, the time of activation of the sterilization case 1-1 can be visualized by the sterilization meter 64 to be checked.

On the other hand, the alternate-current voltage of 100 V from the power source 65 is converted by the direct-current conversion circuit 62 to a direct-current voltage of, for example, 5 V and, as shown in FIG. 10, the direct-current voltage is supplied to the smartphone 100 through the male connector 7 and the female connector 101. That is, the smartphone 100 is sterilized and charged at one time.

In this power-on state, as shown in FIG. 5, the timer has been activated by the controller 63f. After a predetermined period of time during which the sterilization and charging are considered to have been accomplished sufficiently, the controller 63f then disconnects the fixed terminal 63c electrically from the boosting circuit 61, the direct-current conversion circuit 62, and the sterilization meter 64 to complete the sterilization and charging.

After confirming that the sterilization has been completed, the user slides the cover body 3 in the state shown in FIG. 10 (c) leftward as shown in FIG. 10 (b). This causes the pressing force from the cover body 3 on the pin body 63a to be released and thereby the power source to be turned off. As a result, the controller 63f resets the timer and again connects the fixed terminal 63c electrically to the boosting circuit 61, the direct-current conversion circuit 62, and the sterilization meter 64.

Then, as shown in FIG. 10 (a), removing the cover body 3 from the case main body 2 allows the smartphone 100, which has been sterilized and charged, to be taken out of the sterilization case 1-1.

Second Embodiment

Next will be described a second embodiment of the present invention.

Figure 14:
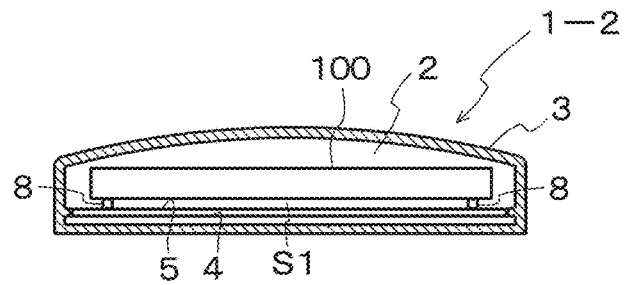
FIG. 14 is a cross-sectional view of a sterilization case according to a second embodiment of the present invention.

FIG. 14 is a cross-sectional view of a sterilization case 1-2 according to the second embodiment of the present invention.

As shown in FIG. 14, the sterilization case 1-2 according to this embodiment differs from the above-described first embodiment in that spacers 8 are provided.

That is, the multiple spacers 8 are disposed on the electrode sheet 5 of the case main body 2. Specifically, four or more spacers 8 are fastened onto the electrode sheet 5 to support thereon the four corners of the lower surface of the loaded smartphone 100.

With the arrangement above, a clearance S1 is formed between the lower surface of the smartphone 100 and the electrode sheet 5, and a large amount of air gains entrance also into the clearance S1.

This allows a large amount of oxygen to be secured over the electrode sheet 5 and thereby the rate of ozone generation by the electrode sheet 5 to increase.

Since the other configurations, operations, and effects are the same as those in the above-described first embodiment, the description thereof will be omitted.

Third Embodiment

Next will be described a third embodiment of the present invention.

Figure 15:
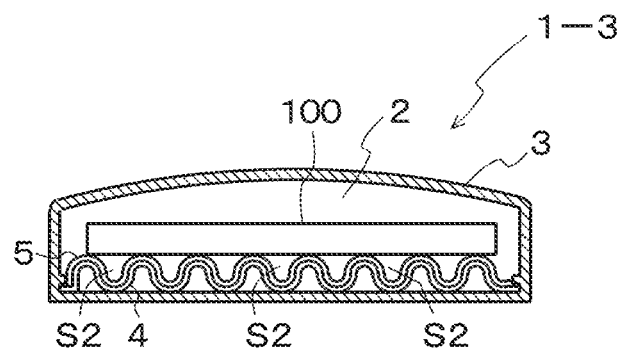
FIG. 15 is a cross-sectional view of a sterilization case according to a third embodiment of the present invention.

FIG. 15 is a cross-sectional view of a sterilization case 1-3 according to the third embodiment of the present invention.

As shown in FIG. 15, the sterilization case 1-3 according to this embodiment differs from the above-described first and second embodiments in the shape of the loading part 4 and the electrode sheet 5.

That is, the loading part 4 is curved to have a waved cross-sectional shape, and a flexible electrode sheet 5 is laid along the shape of the loading part 4.

With the arrangement above, a number of clearances S2 are formed between the lower surface of the smartphone 100 and the waved electrode sheet 5, and a large amount of air fills the clearances S2.

This allows a large amount of oxygen to be secured around the electrode sheet 5 and thereby the rate of ozone generation by the electrode sheet 5 to increase.

Further, the electrode sheet 5, which is thus laid in a waved shape, can have a large area.

Since the other configurations, operations, and effects are the same as those in the above-described first and second embodiments, the description thereof will be omitted.

Fourth Embodiment

Next will be described a fourth embodiment of the present invention.

Figure 16:
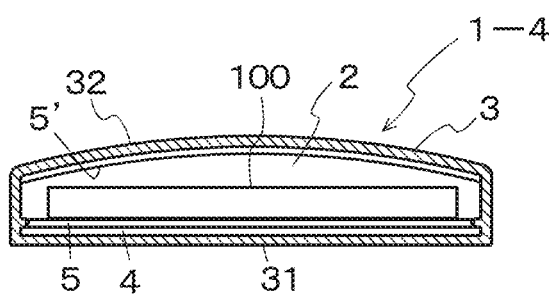
FIG. 16 is a cross-sectional view of a sterilization case according to a fourth embodiment of the present invention.

FIG. 16 is a cross-sectional view of a sterilization case 1-4 according to the fourth embodiment of the present invention.

As shown in FIG. 16, the sterilization case 1-4 according to this embodiment differs from the above-described first to third embodiments in that an electrode sheet 5' separate from the electrode sheet 5 is provided.

Specifically, the electrode sheet 5' is laid on the inner surface of the top wall 32 of the cover body 3.

Figure 17:
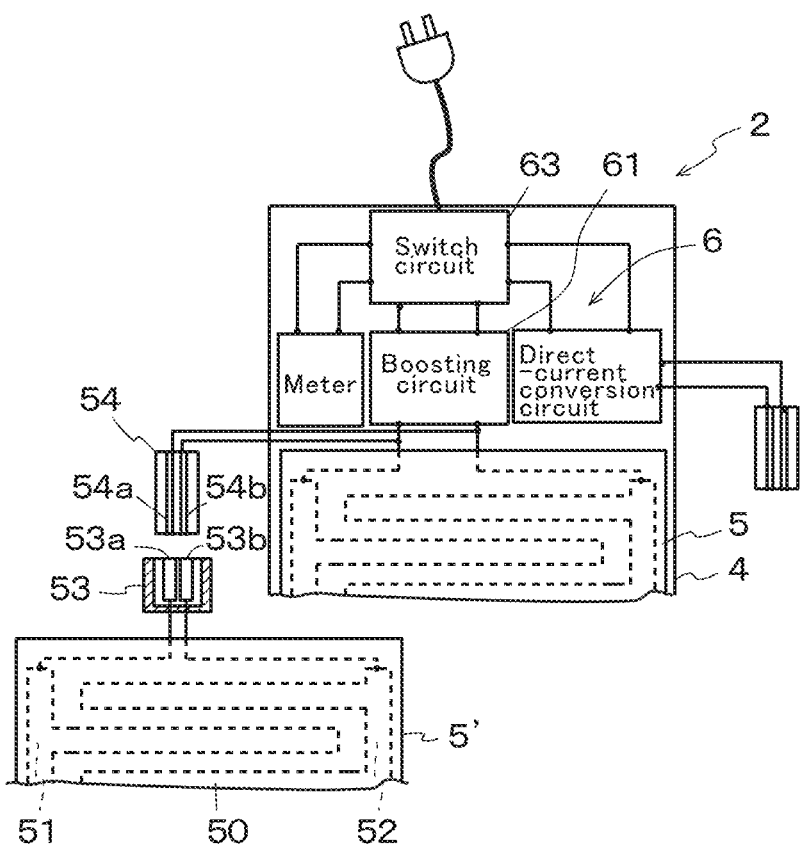
FIG. 17 is a schematic plan view showing an electrical connection structure between an electrode sheet and a boosting circuit.

FIG. 17 is a schematic plan view showing an electrical connection structure between the electrode sheet 5' and the boosting circuit 61.

As shown in FIG. 17, the electrode sheet 5' has the same structure as the electrode sheet 5, having a dielectric 50 and electrodes 51, 52. Moreover, terminals 53a, 53b of a female connector 53 are connected to the electrodes 51, 52 of the electrode sheet 5', while terminals 54a, 54b of a male connector 54 are connected to the output terminals of the boosting circuit 61. This causes, when the male connector 54 is inserted into the female connector 53, the terminals 53a, 53b of the female connector 53 and the terminals 54a, 54b of the male connector 54 to come into contact with each other, whereby the boosting circuit 61 and the electrodes 51, 52 of the electrode sheet 5' are connected electrically via the female connector 53 and the male connector 54.

Figure 18:
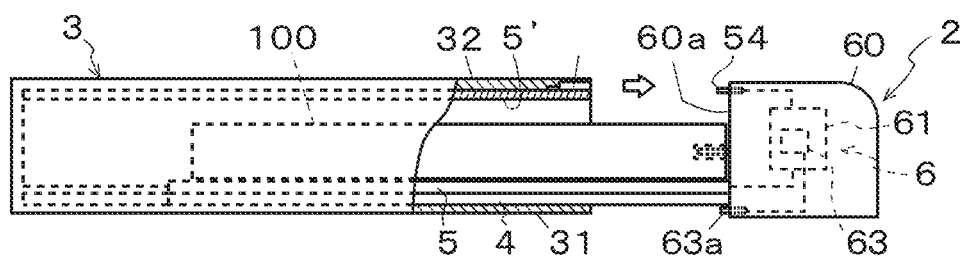
FIG. 18 is a partially cutaway schematic side view of the sterilization case.

FIG. 18 is a partially cutaway schematic side view of the sterilization case 1-4 according to this embodiment.

As shown in FIG. 18, the electrode sheet 5' is applied on the inner surface of the top wall 32 of the cover body 3 and the female connector 53 is attached in the rear of the top wall 32. On the other hand, the male connector 54 connected to the boosting circuit 61 is provided in a manner protruding on an upper part of the front wall 60a of the voltage supplying part 6.

Since the sterilization case 1-4 is thus configured, when the cover body 3 is fitted to the loading part 4 of the case main body 2 to which the smartphone 100 is connected and moved toward the housing part 60, the female connector 53 of the electrode sheet 5' comes close to the male connector 54 of the housing part 60. When the cover body 3 is then brought closest to the housing part 60, the male connector 54 is inserted into the female connector 53. As a result, the boosting circuit 61 of the voltage supplying part 6 and the electrodes 51, 52 of the electrode sheet 5' are connected electrically via the female connector 53 and the male connector 54.

In this state, since the power source is on with the movement of the pin body 63a, an alternate-current voltage or a pulsed voltage is supplied from the boosting circuit 61 to the electrodes 51, 52 of both the electrode sheet 5 and the electrode sheet 5'. This causes ozone to be emitted from the upper electrode sheet 5' and the lower electrode sheet 5 toward the smartphone 100, whereby the smartphone 100 is sterilized in a short period of time.

Since the other configurations, operations, and effects are the same as those in the above-described first to third embodiments, the description thereof will be omitted.

Fifth Embodiment

Next will be described a fifth embodiment of the present invention.

Figure 19:
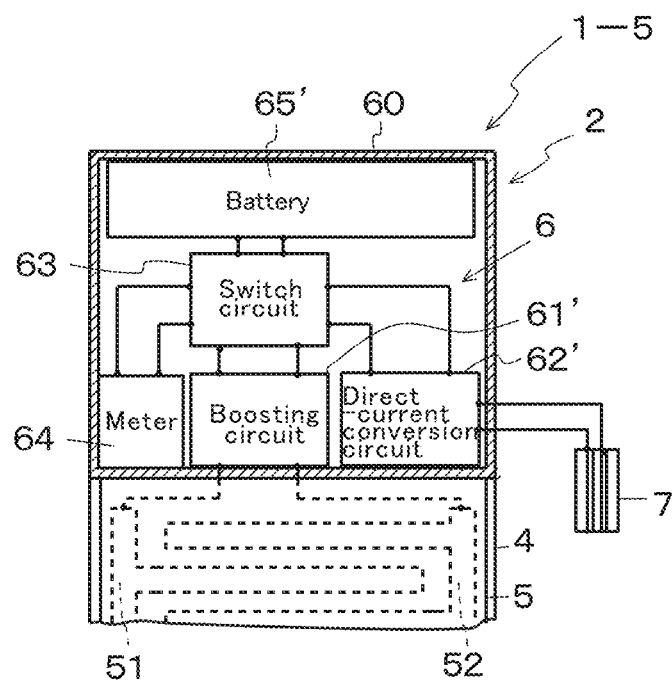
FIG. 19 is a cutaway schematic cross-sectional view of a case main body of a sterilization case according to a fifth embodiment of the present invention.

FIG. 19 is a cutaway schematic cross-sectional view of a case main body 2 of a sterilization case 1-5 according to the fifth embodiment of the present invention.

As shown in FIG. 19, the sterilization case 1-5 according to this embodiment differs from the above-described first to fourth embodiments in that the power source is a battery 65' serving as a direct-current power source.

In this embodiment, the battery 65' is a dry cell capable of supplying a direct-current voltage of, for example, 6 V and can be housed within the housing part 60 of the case main body 2.

The battery 65' is connected via the switch circuit 63 to a boosting circuit 61', a direct-current conversion circuit 62', and the sterilization meter 64.

The boosting circuit 61' has a function of boosting the direct-current voltage of 6 V from the battery 65' to an alternate-current voltage or a pulsed voltage of 2 kV to 10 kV, and the direct-current conversion circuit 62' has a function of converting the direct-current voltage of 6 V from the battery 65' into a direct-current voltage of 5 V.

With the arrangement above, the direct-current voltage of 6 V from the battery 65' is converted by the boosting circuit 61' into an alternate-current voltage or a pulsed voltage of 2 kV to 10 kV. The alternate-current voltage or the pulsed voltage is then supplied from the boosting circuit 61' to the electrodes 51, 52 of the electrode sheet 5. At the same time, the direct-current voltage of 6 V from the battery 65' is converted by the direct-current conversion circuit 62' into a direct-current voltage of 5 V and supplied to the male connector 7.

Since the other configurations, operations, and effects are the same as those in the above-described first to fourth embodiments, the description thereof will be omitted.

Sixth Embodiment

Next will be described a sixth embodiment of the present invention.

Figure 20:
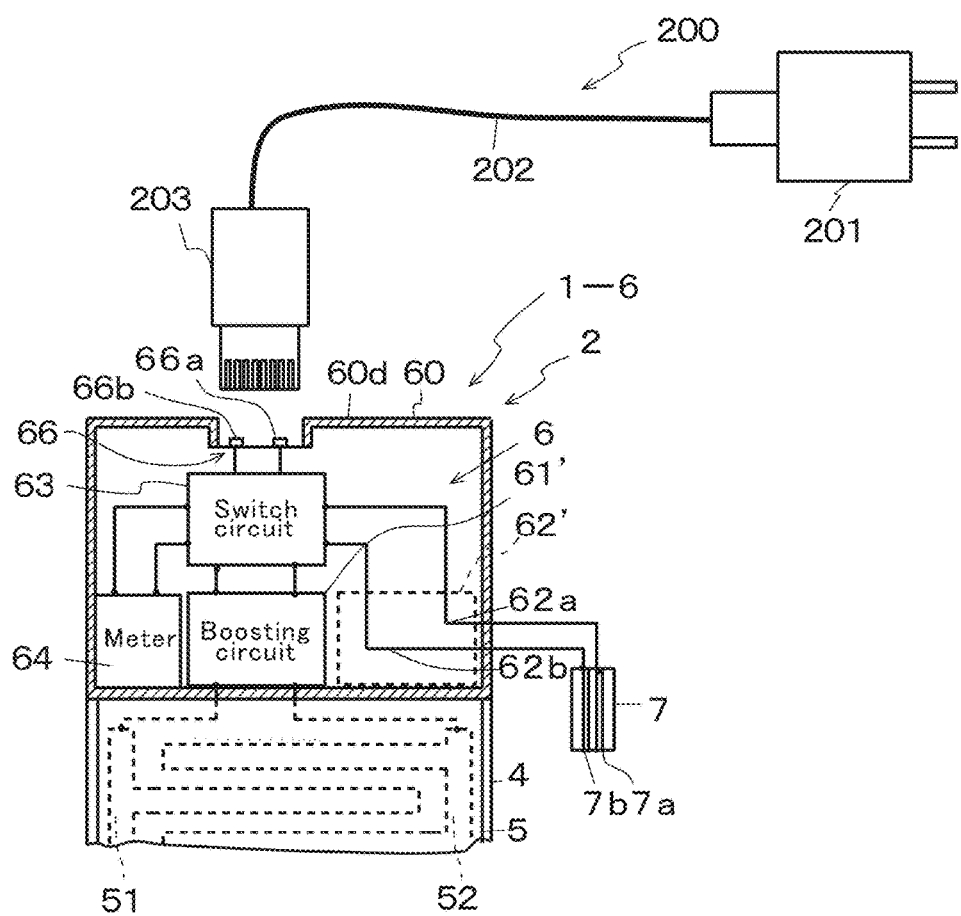
FIG. 20 is a cutaway schematic cross-sectional view of a case main body of a sterilization case according to a sixth embodiment of the present invention.

FIG. 20 is a cutaway schematic cross-sectional view of a case main body 2 of a sterilization case 1-6 according to the sixth embodiment of the present invention.

As shown in FIG. 20, the sterilization case 1-6 according to this embodiment differs from the above-described first to fifth embodiments in that the direct-current conversion circuit 62" has a structure for supplying the direct-current power source voltage directly to the male connector 7.

Specifically, a female connector 66 is provided in a rear wall 60d of the housing part 60 of the voltage supplying part 6 and electrically connected via the switch circuit 63 to a boosting circuit 61", the direct-current conversion circuit 62", and the sterilization meter 64.

The direct-current conversion circuit 62" is a circuit for outputting the direct-current power source from the female connector 66 directly with no conversion to the male connector 7 and formed by wires 62a, 62b themselves.

The power source according to this embodiment is a 5 V direct-current power source supplied from a well-known charger 200 used for the smartphone 100.

Specifically, the charger 200 includes a converter 201 for converting the 100V commercial voltage into a direct-current voltage of 5 V, a cable 202 drawn out of the converter 201, and a USB connector 203 attached to a leading end portion of the cable 202.

When the USB connector 203 of the charger 200 is inserted into the female connector 66 of the case main body 2, power source terminals (not shown) of the USB connector 203 come into contact with terminals 66a, 66b of the female connector 66.

With the arrangement above, when the converter 201 of the charger 200 is connected to the commercial power source socket and the USB connector 203 is connected to the female connector 66 of the case main body 2, the 5 V direct-current voltage from the USB connector 203 is supplied to the boosting circuit 61", the direct-current conversion circuit 62", and the sterilization meter 64 when the switch circuit 63 is on. The 5 V direct-current voltage is then converted by the boosting circuit 61" into an alternate-current voltage or a pulsed voltage of 2 kV to 10 kV, while supplied by the direct-current conversion circuit 62" directly as a 5 V direct-current voltage to the male connector 7.

Since the other configurations, operations, and effects are the same as those in the above-described first to fifth embodiments, the description thereof will be omitted.

Seventh Embodiment

Next will be described a seventh embodiment of the present invention.

Figure 21:
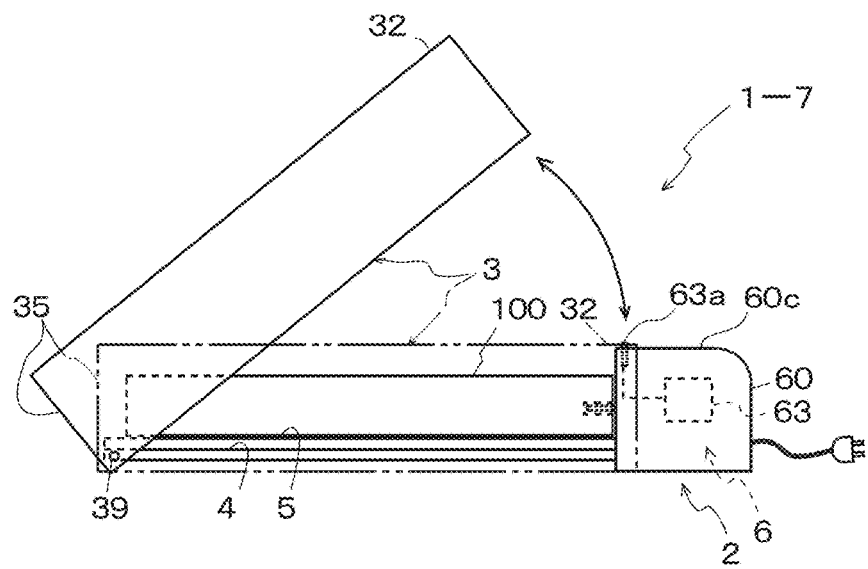
FIG. 21 is a schematic side view of a sterilization case according to a seventh embodiment of the present invention.

FIG. 21 is a schematic side view of a sterilization case 1-7 according to the seventh embodiment of the present invention.

The above-described first to sixth embodiments are arranged such that the cover body 3 can be slid and fitted to the case main body 2. The sterilization case 1-7 according to this embodiment differs from the above-described first to sixth embodiments in that the cover body 3 is fitted rotatably to the case main body 2, as shown in FIG. 21.

Specifically, a lower part of the front wall 35 of the cover body 3 is fitted rotatably using a shaft 39 to the front (left in FIG. 21) of the loading part 4 of the case main body 2.

Moreover, the pin body 63a of the switch circuit 63 is attached onto the top wall 60c of the housing part 60 of the case main body 2.

With the arrangement above, the cover body 3 can be opened to load the smartphone 100 on the case main body 2 as indicated by the solid line in FIG. 21. The cover body 3 can then be closed to confine the smartphone 100 within the sterilization case 1-7 as indicated by the alternate long and two short dashed line in FIG. 21. When the cover body 3 is thus closed, the top wall 32 of the cover body 3 presses the pin body 63a, whereby the power source is turned on.

Since the other configurations, operations, and effects are the same as those in the above-described first to sixth embodiments, the description thereof will be omitted.

Eighth Embodiment

Next will be described an eighth embodiment of the present invention.

Figure 22:
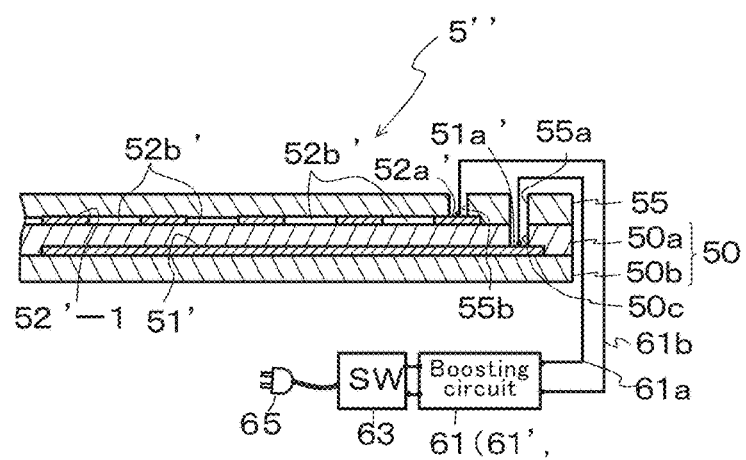
FIG. 22 is a cross-sectional view showing a substantial part of a sterilization case according to an eighth embodiment of the present invention.
Figure 23:
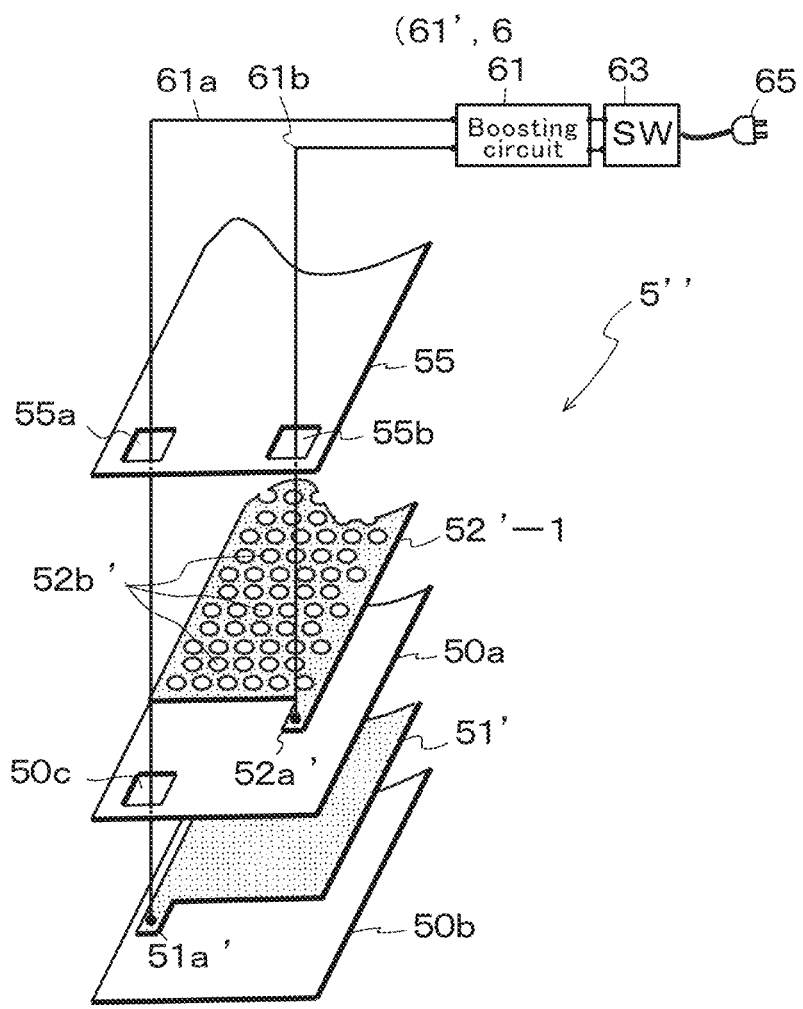
FIG. 23 is an exploded perspective view of the substantial part shown in FIG. 22.

FIG. 22 is a cross-sectional view showing a substantial part of a sterilization case according to the eighth embodiment of the present invention, and FIG. 23 is an exploded perspective view of the substantial part shown in FIG. 22.

As shown in FIG. 22, the sterilization case according to this embodiment includes an electrode sheet 5" having a structure different from those of the electrode sheets 5, 5' according to the above-described embodiments.

That is, only one electrode 51' is housed within the dielectric 50 and the other electrode 52'-1 is provided on the surface of the dielectric 50.

Specifically, as shown in FIG. 23, the solid electrode 51' is formed in a laminated manner on the lower dielectric layer 50b and the upper dielectric layer 50a is laminated on the dielectric layer 50b in a manner covering the electrode 51'. Moreover, the electrode 52'-1 having approximately the same shape as the electrode 51' is formed on the dielectric layer 50a. Further, a protective layer 55 is laminated on the electrode 52'-1.

A terminal part 51a' is provided at a corner of the electrode 51' and a rectangular feed port 50c through which the terminal part 51a' is exposed is formed at a corner of the upper dielectric layer 50a. Further, a feed port 55a in communication with the feed port 50c is provided at a corner of the protective layer 55. Moreover, a wire 61a extending from one of the output terminals of the boosting circuit 61 is connected to the terminal part 51a' of the electrode 51' through the feed ports 55a and 50c.

On the other hand, a terminal part 52a' is provided at a corner of the electrode 52'-1 and a rectangular feed port 55b through which the terminal part 52a' is exposed is formed at a corner of the upper protective layer 55. Moreover, a wire 61b extending from the other output terminal of the boosting circuit 61 is connected to the terminal part 52a' of the electrode 52'-1 through the feed port 55b.

Further, a number of circular holes 52b' are bored at a regular interval in the electrode 52'-1 that is provided on the surface of the dielectric 50.

Like the electrode sheet 5 according to the above-described first embodiment, the electrode sheet 5" according to this embodiment is also formed entirely of polymeric resin. That is, not only are the dielectric layers 50a, 50b and the protective layer 55 respectively formed of polyimide resin, but the electrodes 51', 52'-1 are also formed of conductive polymer, an example of polymeric resin.

It is noted that in this embodiment, the protective layer 55, which is provided on the electrode 52'-1 existing on the surface of the dielectric 50, is not an essential member and, in some cases, may not necessarily be provided.

Figure 24A:
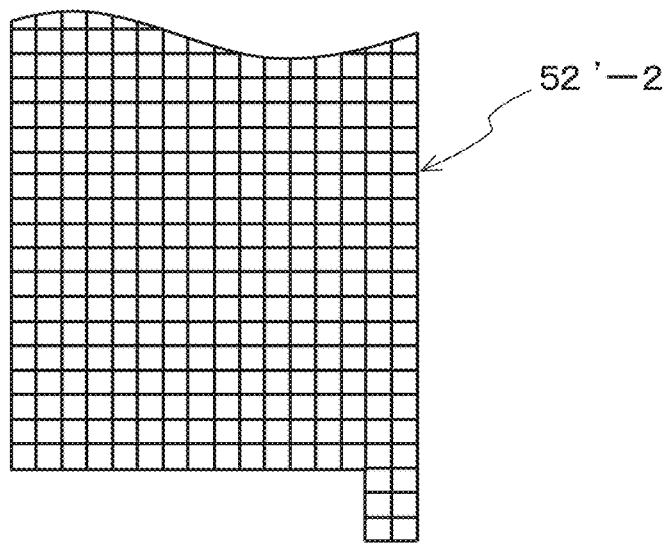
FIGS. 24(a) and 24(b) are plan views showing variations of electrodes according to the eighth embodiments.
Figure 24B:
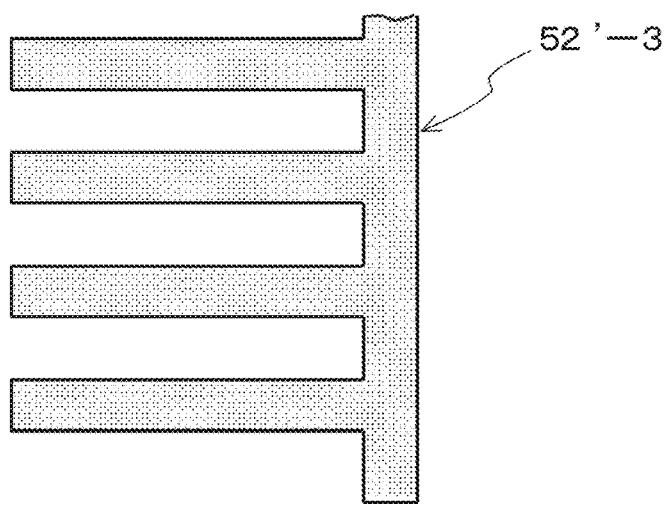

While in this embodiment, the electrode 52'-1 having a number of circular holes 52b' are applied as the other electrode, a meshed electrode 52'-2 may be applied as the other electrode as shown in FIG. 24 (a) or a comb-like electrode 52'-3 may be applied as the other electrode as shown in FIG. 24 (b).

Since the other configurations, operations, and effects are the same as those in the above-described first to seventh embodiments, the description thereof will be omitted.

Ninth Embodiment

Next will be described a ninth embodiment of the present invention.

Figure 25:
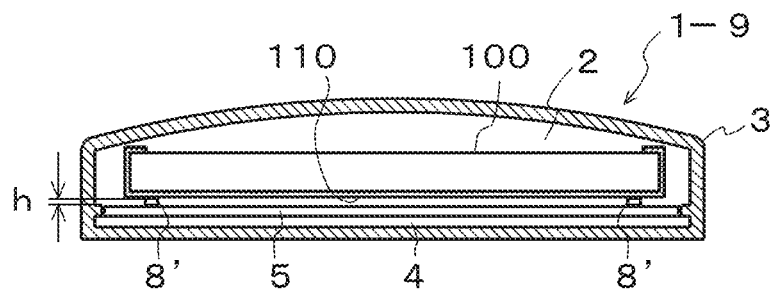
FIG. 25 is a cross-sectional view showing a substantial part of a sterilization case according to a ninth embodiment of the present invention.
Figure 26:
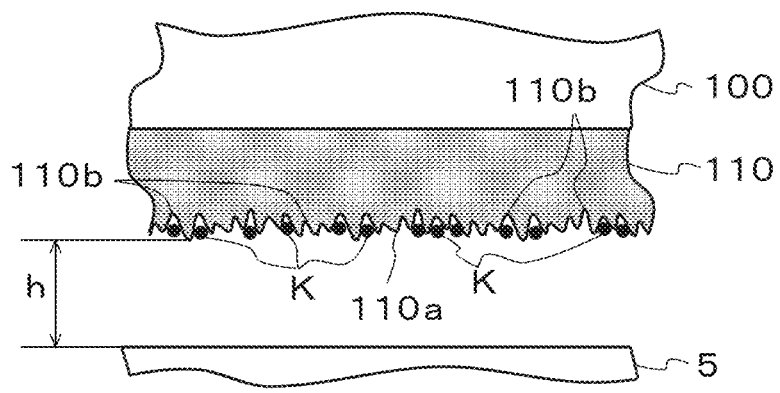
FIG. 26 is a partially enlarged cross-sectional view illustrating the sterilization mechanism.

FIG. 25 is a cross-sectional view showing a substantial part of a sterilization case according to the ninth embodiment of the present invention, and FIG. 26 is a partially enlarged cross-sectional view illustrating the sterilization mechanism.

As shown in FIG. 25, the sterilization case 1-9 according to this embodiment differs from the above-described first to eighth embodiments in that a structure is employed for maintaining the distance "h" between the sterilization target surface and the electrode sheet 5 at a constant value.

That is, in this embodiment, a spacer 8' serving as a maintaining part is set to have a height "h" within a range of 10 mm or less.

If the surface of the smartphone 100 is mirrored as shown in the above-described second embodiment, etc., bacteria on the surface of the smartphone 100 can be removed almost completely by ozone regardless of the distance between the smartphone 100 and the electrode sheet 5.

However, if the surface of the smartphone 100 is textured or if the smartphone 100 housed within a case made of textured material or cloth is sterilized, the larger the distance between the surface of the smartphone 100 or the surface of the case to be sterilized and the electrode sheet 5, the less the sterilization effect can be achieved.

Hence, in this embodiment, the height "h" of the spacer 8' is set within a range of 10 mm or less to position the sterilization target close to the electrode sheet 5 and thereby to achieve a high sterilization effect even if the surface of the smartphone 100 may be textured or the case may be made of textured material or cloth.

Specifically, four or more spacers 8' are fastened onto the electrode sheet 5 such that the distance "h" between the sterilization target and the electrode sheet 5 is maintained within a range of 10 mm or less.

With the arrangement above, as shown in FIG. 25, when the smartphone 100 is housed within a case 110 (mobile communication device case) made of textured material or cloth and the case 110 is loaded on the spacer 8', the distance "h" between the surface of the case 110 and the electrode sheet 5 is maintained within a range of 10 mm or less.

In this state, when the cover body 3 is fitted to the case main body 2 and ozone is generated, the ozone fills the clearance between the case 110 and the electrode sheet 5 to try to remove bacteria attached to the surface of the case 110.

However, if the surface of the case 110 is textured, most of the bacteria K gain entrance into a number of recessed portions 110b in the surface 110a of the case 110, as shown in FIG. 26. Accordingly, if the distance "h" between the surface 110a of the case 110 and the electrode sheet 5 is large, the ozone cannot remove the bacteria K within the recessed portions 110b, resulting in a significant reduction in the sterilization effect.

However, in this embodiment, since the distance "h" between the surface 110a of the textured case 110 and the electrode sheet 5 is maintained by the spacer 8' within a range of 10 mm or less to cause the surface 110a of the case 110 to face the electrode sheet 5 in the vicinity thereof, the bacteria K within the recessed portions 110b can be removed reliably by the ozone.

The inventors have conducted the following experiment to demonstrate the effect.

Figure 27:
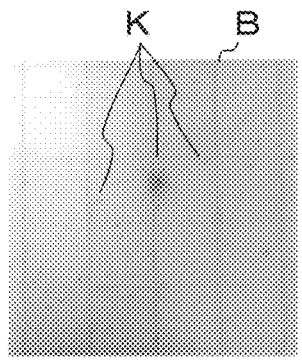
FIGS. 27(a), 27(b), 27(c), 27(d), 27(e) and 27(f) are transferred views of photos showing viability states of bacteria.
Figure 27:
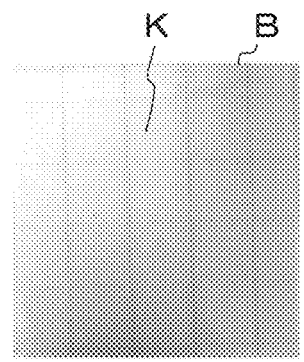
Figure 27:
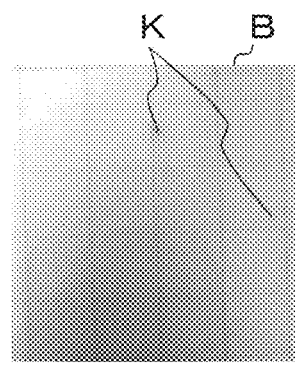
Figure 27:
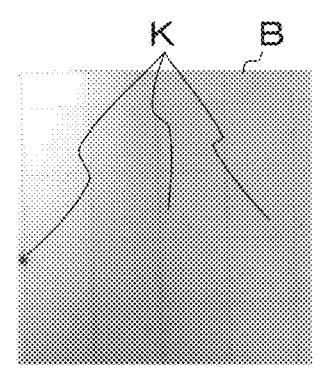
Figure 27:
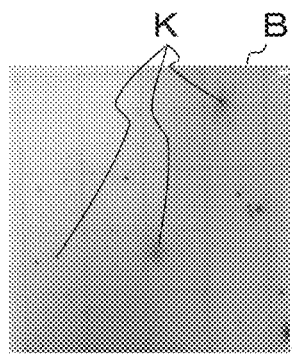
Figure 27:
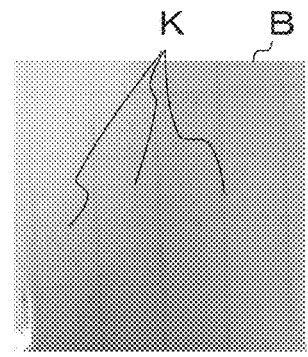

FIG. 27 is a transferred view of photos showing viability states of bacteria K.

The inventors have conducted the experiment under a common indoor condition.

First, microorganisms (common viable bacteria; hereinafter referred to as "bacteria K") were preparatorily grown separately and the bacteria K were sprayed onto a piece of polyester cotton blended cloth not shown, and then the cloth was dried.

The surface of the prepared cloth was then wiped with a 5 cm square medium B, and the bacteria K were grown on the medium B under a temperature of 35 degrees C. for 48 hours. Then, as shown in FIG. 27 (*a*), 137 bacteria K lived on the 5 cm square medium B.

That is, it was ensured that the number of living bacteria K was 137 with no ozone treatment.

Next, the prepared cloth was fixed "x" mm immediately above the electrode sheet 5 with the surface on which the bacteria K were sprayed facing the electrode sheet 5. In this state, ozone was generated from the electrode sheet 5 and the cloth was exposed to the ozone for two hours. Upon this, a pulsed power source of p-p 14 kV at a frequency of 13 Hz was supplied to the electrode sheet 5 to generate ozone.

Thereafter, the surface of the ozone-treated cloth was then wiped with a 5 cm square medium B, and the bacteria K were grown on the medium B under a temperature of 35 degrees C. for 48 hours.

The distance "x" mm between the cloth and the electrode sheet 5 was set to 2 mm, 5 mm, 10 mm, 20 mm, 30 mm for the ozone treatment. As a result, the number of living bacteria K on the 5 cm square medium B was 1 as shown in FIG. 27 (*b*) if the distance between the cloth and the electrode sheet 5 was 2 mm, the number of living bacteria K was 19 as shown in FIG. 27 (*c*) if the distance was 5 mm, the number of living bacteria K was 51 as shown in FIG. 27 (*d*) if the distance was 10 mm, the number of living bacteria K was 103 as shown in FIG. 27 (*e*) if the distance was 20 mm, and the number of living bacteria K was 102 as shown in FIG. 27 (*f*) if the distance was 30 mm.

That is, it was ensured that with an ozone treatment, the larger the distance between the cloth and the electrode sheet 5, the larger the number of living bacteria K became.

Figure 28:
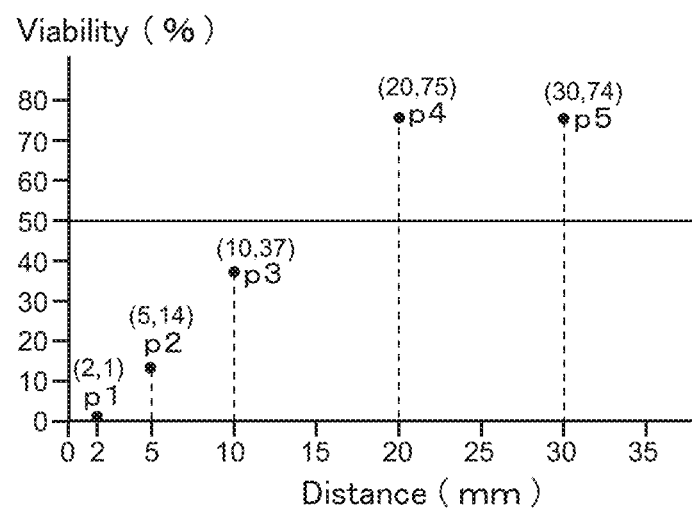
FIG. 28 is a diagrammatic view showing the relationship between the viability of bacteria and the distance.

FIG. 28 is a diagrammatic view showing the relationship between the viability of bacteria K and the distance.

The inventors defined the viability of bacteria K as (number of bacteria after ozone treatment number of bacteria before ozone treatment)×100(%), and plotted the relationship between the electrode sheet/cloth distance and the viability of bacteria K in the above-described ozone treatment.

As shown in FIG. 28, points p1 to p5 were then obtained. As indicated by the points p1, p2, p3, the viability is 1%, 14%, 37% for the distance 2 mm, 5 mm, 10 mm, being less than a reference viability of 50%.

However, as indicated by the points p4, p5, the viability is 75%, 74% for the distance 20 mm, 30 mm, being far over the reference viability of 50%.

From the experimental result, it can be determined that the distance between the cloth and the electrode sheet 5 at which the viability reliably falls below 50% is 10 mm or less.

Hence, the inventors set the distance "h" to be maintained by the spacer 8' shown in FIG. 25 within a range of 10 mm or less. Thus maintaining the distance "h" between the surface 110a of the case 110 and the electrode sheet 5 within a range of 10 mm or less allows the viability of bacteria K living on the surface 110a of the case 110 to be limited below the reference viability of 50%, as shown in FIG. 28.

Figure 29:
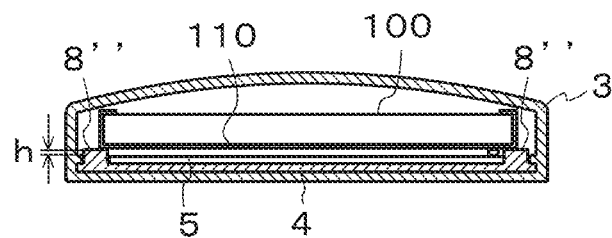
FIG. 29 is a cross-sectional view showing a substantial part of a sterilization case according to a variation of the ninth embodiment.

It is noted that while in this embodiment, the spacer 8' provided in a manner protruding on the electrode sheet 5 is applied as a maintaining part, the maintaining part is not limited to only such a spacer 8'. As shown in FIG. 29, a spacer 8" formed by projecting upward the corners of the loading part 4 is also included.

Since the other configurations, operations, and effects are the same as those in the above-described first to eighth embodiments, the description thereof will be omitted.

It is noted that the present invention is not intended to be limited to the above-described embodiments, but may be variously varied and changed within the spirit and scope of the invention.

For example, while in the above-described embodiments, the electrodes 51, 52, 51', 52'-1 to 52'-3 of the electrode sheets 5, 5" are also formed of conductive polymer, an example of polymeric resin like the dielectric 50, the electrodes 51, 52, 51', 52'-1 to 52'-3 may be formed of metal foil such as copper or conductive ink such as carbon or silver.

Also, while the electrode sheets 5, 5' according to the above-described first to seventh embodiments employ the structure in which the pair of comb-like electrodes 51, 52 are housed together within the dielectric 50 and the electrode sheet 5" according to the above-described eighth embodiment employs the structure in which the one electrode 51' is housed within the dielectric 50 and the other electrode 52'-1 is provided on the surface of the dielectric 50, the structure of the electrode sheet is not limited thereto. For example, a pair of electrodes may be formed in a flat-plate manner and the two electrodes may be arranged side by side at a regular interval or single electrodes may be formed together in a spiral shape and the pair of spiral electrodes may be fitted to each other at a regular interval.

Also, while the above-described embodiments illustrate the sterilization cases 1-1 to 1-7 including the sterilization meter 64, it will be appreciated that sterilization cases not including the sterilization meter 64 also fall within the scope of the invention.

Also, while the above-described embodiments illustrate the smartphone 100 as an example mobile communication device, it will be appreciated, without being limited thereto, that cell phones such as so-called Galapagos cell phones and common cell phones are also included in such a mobile communication device.

REFERENCE SIGNS LIST 1-1 to 1-7, 1-9 . . . sterilization case, 2 . . . case main body, 3 . . . cover body, 4 . . . loading part, 5, 5', 5" . . . electrode sheet, 6 . . . voltage supplying part, 7, 54 . . . male connector, 7*a*, 7*b* . . . power source terminal, 53*a*, 53*b*, 54*a*, 54*b*, 66*a*, 66*b* . . . terminal, 8, 8', 8" . . . spacer, 30 . . . opening, 31 . . . bottom wall, 32 . . . top wall, 33, 34 . . . side wall, 33*a*, 34*a* . . . groove, 35 . . . front wall, 39 . . . shaft, 50 . . . dielectric, 50*a*, 50*b* . . . dielectric layer, 50*c*, 55*a*, 55*b* . . . feed port, 51, 52, 51', 52'-1 to 52'-3 . . . electrode, 51*a*, 52*a* . . . comb teeth, 51*a'*, 52*a'* . . . terminal part, 52*b'* . . . circular hole, 53, 66, 101 . . . female connector, 55 . . . protective layer, 60 . . . housing part, 60*a* . . . front wall, 60*b* . . . hole, 60*c* . . . top wall, 60*d* . . . rear wall, 61, 61', 61" . . . boosting circuit, 61*a*, 61*b* . . . wire, 62, 62', 62" . . . direct-current conversion circuit, 62*a*, 62*b* . . . wire, 63 . . . switch circuit, 63*a* . . . pin body, 63*b* . . . spring, 63*c* . . . fixed terminal, 63*d* . . . movable terminal, 63*e* . . . stopper, 63*f* . . . controller, 64 . . . sterilization meter, 65 . . . power source, 65' . . . battery, 100 . . . smartphone, 110 . . . case, 110*a* . . . surface, 110*b* . . . recessed portion, 200 . . . charger, 201 . . . converter, 202 . . . cable, 203 . . . USB connector, B . . . medium, h . . . distance, K . . . bacteria, S1, S2 . . . clearance.

The invention claimed is:

1. A sterilization case comprising:
a case main body having a loading part with a surface on which an electrode sheet is laid, the electrode sheet being formed by housing at least one of a pair of electrodes within a sheet-like dielectric, and in which a mobile communication device can be loaded on the electrode sheet, and a voltage supplying part supplying a predetermined voltage to the electrode sheet and the mobile communication device; and
a cover body attached to the case main body in an openable and closable manner, wherein
the voltage supplying part comprises:
a first circuit of converting a power source into a voltage, the first circuit supplying the voltage to the pair of electrodes so that ozone is generated through the at least one of the pair of electrodes; and
a second circuit of converting the power source into a power source voltage of the mobile communication device, the second circuit supplying the power source voltage to a male connector connectable to a female connector of power supply to the mobile communication device.

2. The sterilization case according to claim 1, wherein
another electrode sheet separate from the electrode sheet is provided on an inner surface of a top wall of the cover body, and wherein
the first circuit is connected also to electrodes of the another separate electrode sheet.

3. The sterilization case according to claim 1, wherein
a spacer for loading the mobile communication device is provided in a manner protruding on the electrode sheet on the loading part.

4. The sterilization case according to claim 1, wherein
the loading part is formed to have a waved cross-sectional shape and the electrode sheet is laid along the waved loading part.

5. The sterilization case according to claim 1, wherein
the power source is an alternate-current power source, and wherein
the first circuit is a circuit for converting the alternate-current voltage of the power source into an alternate-current voltage or a pulsed voltage of a desired value and supplying the voltage to the pair of electrodes, and wherein
the second circuit is a circuit for converting the alternate-current voltage of the power source into a direct-current voltage of a desired value and supplying the voltage to the male connector.

6. The sterilization case according to claim 1, wherein
the power source is a direct-current power source, and wherein
the first circuit is a circuit for converting the direct-current voltage of the power source into an alternate-current voltage or a pulsed voltage of a desired value and supplying the voltage to the pair of electrodes, and wherein
the second circuit is a circuit for converting the direct-current voltage of the power source into a direct-current voltage of a desired value and supplying the voltage to the male connector.

7. The sterilization case according to claim 6, wherein
the second circuit is a circuit for supplying the direct-current voltage of the power source directly to the male connector.

8. The sterilization case according to claim 1, wherein
at least the dielectric of the electrode sheet is formed of polymeric resin.

9. The sterilization case according to claim 1, wherein
a switch mechanism is provided on the case main body, the switch mechanism being capable of turning on the power source only when the cover body is closed and turning off the power source after a predetermined period of sterilization time with the power source on.

10. The sterilization case according to claim 1, wherein
a sterilization meter for displaying sterilization processing time is provided on the case main body.

11. The sterilization case according to claim 1, wherein
each of the pair of electrodes is formed in a comb shape and comb teeth of the pair of electrodes are engaged with each other at a regular interval.

12. The sterilization case according to claim 1, wherein
one of the pair of electrodes is housed within the dielectric and another electrode with a number of holes or in a comb shape is disposed on a surface of the dielectric in a manner opposed to the one electrode.

13. The sterilization case according to claim 1, wherein
the loading part is provided with a maintaining part for maintaining a distance between the electrode sheet and the mobile communication device or a case of the mobile communication device loaded on the loading part within a range of 10 mm or less.

* * * * *